United States Patent
Chen (10) Patent No.: US 12,220,253 B2
(45) Date of Patent: Feb. 11, 2025

(54) SYSTEMS AND METHODS FOR DETECTING GLUCOSE METABOLISM BY A PATIENT

(71) Applicant: GE Precision Healthcare LLC, Wauwatosa, WI (US)

(72) Inventor: Albert Po Fu Chen, Toronto (CA)

(73) Assignee: GE Precision Healthcare LLC, Wauwatosa, WI (US)

( * ) Notice: Subject to any disclaimer, the term of this patent is extended or adjusted under 35 U.S.C. 154(b) by 297 days.

(21) Appl. No.: 17/092,850

(22) Filed: Nov. 9, 2020

(65) Prior Publication Data

US 2022/0142567 A1    May 12, 2022

(51) Int. Cl.
| | | |
|---|---|---|
| *A61B 5/00* | (2006.01) | |
| *A61B 5/055* | (2006.01) | |
| *A61B 5/145* | (2006.01) | |
| *G01R 33/561* | (2006.01) | |

(52) U.S. Cl.
CPC ............ *A61B 5/4866* (2013.01); *A61B 5/055* (2013.01); *A61B 5/14532* (2013.01); *G01R 33/561* (2013.01)

(58) Field of Classification Search
CPC .... A61B 5/4866; A61B 5/055; G01R 33/441; G01R 33/4625; G01R 33/485; G01R 33/50
See application file for complete search history.

(56) References Cited

U.S. PATENT DOCUMENTS

| | | | |
|---|---|---|---|
| 5,042,488 A | | 8/1991 | Ackerman |
| 5,685,300 A | * | 11/1997 | Kuenstner ............ G01R 33/465 436/95 |
| 7,795,868 B2 | | 9/2010 | Larson et al. |
| 8,933,697 B2 | | 1/2015 | Chen et al. |
| 8,968,703 B2 | | 3/2015 | Chen et al. |
| 9,283,317 B2 | | 3/2016 | Lau et al. |
| 10,520,561 B2 | | 12/2019 | Comment et al. |

(Continued)

FOREIGN PATENT DOCUMENTS

WO    2019126642 A1    6/2019

OTHER PUBLICATIONS

Horace S. Isbell, Deuterium Isotope Effects in (alpha)-(beta) Pyranose and Pyranose-Furanose Interconversions1 (Year: 1966).*

(Continued)

*Primary Examiner* — Dixomara Vargas
(74) *Attorney, Agent, or Firm* — Andrus Intellectual Property Law, LLP (57) ABSTRACT

A method for detecting a metabolism of glucose by a patient. The method includes producing a magnetic field that acts upon the patient, then acquiring magnetic resonance data of deuterated water within the patient, where deuterated glucose has been administered to the patient, where the deuterated water is produced during the metabolism of the deuterated glucose by the patient, and where the magnetic resonance data is acquired at a resonant frequency of deuterium. The method further includes analyzing the magnetic resonance data acquired at the resonant frequency of deuterium, non-spectrally resolved, to generate a processed dataset. The method further includes constructing an image based on the processed dataset, where the metabolism of the glucose by the patient is detected via the constructed image.

22 Claims, 5 Drawing Sheets

(56) References Cited

U.S. PATENT DOCUMENTS

| | | | | |
|---|---|---|---|---|
| 2010/0322865 | A1* | 12/2010 | Duerk | A61K 49/10 |
| | | | | 600/431 |
| 2014/0205591 | A1* | 7/2014 | Mickiewicz | G01R 33/465 |
| | | | | 324/309 |
| 2016/0022197 | A1* | 1/2016 | Ramadan | A61B 5/742 |
| | | | | 324/309 |
| 2019/0094316 | A1 | 3/2019 | Comment et al. | |
| 2020/0319279 | A1* | 10/2020 | De Feyter | A61B 5/4094 |
| 2020/0330618 | A1* | 10/2020 | Lesiv | A61K 49/10 |
| 2022/0079905 | A1* | 3/2022 | Lesiv | A61K 31/198 |
| 2023/0126411 | A1* | 4/2023 | Donabedian | G01R 33/56 |
| | | | | 600/420 |

OTHER PUBLICATIONS

Henk M. De Feyter, Deuterium metabolic imaging (DMI) for MRI-based 3D mapping of metabolism in vivo (Year: 2018).*

De Feyter, Henk M. et al. Deuterium metabolic imaging (DMI) for MRI-based 3D mapping of metabolism in vivo. Science Advances. 2018:4. 11 pages.

Cope, Freeman W. Nuclear Magnetic Resonance Evidence Using D2O for Structured Water in Muscle and Brain. Biophysical Journal. vol. 9, 1969. pp. 303-319.

Mahar, Rohit et al. HDO production from [2H7]glucose Quantitatively Identifies Warburg Metabolism. Scientific Reports. (2020) 10:8885. 10 pages.

Lu, Ming et al. Quantitative assessment of brain glucose metabolic rates using in vivo deuterium magnetic resonance spectroscopy. Journal of Cerebral Blood Flow & Metabolism. 2017, vol. 37(11). pp. 3518-3530.

* cited by examiner

SYSTEMS AND METHODS FOR DETECTING GLUCOSE METABOLISM BY A PATIENT

FIELD

The present disclosure generally relates to systems and methods for detecting glucose uptake in a patient, and more particularly to detecting deuterated glucose and its uptake and metabolism using magnetic resonance imaging without spectrally resolved data.

BACKGROUND

The present disclosure generally relates to the use of magnetic resonance (MR) spectroscopy and magnetic resonance imaging (MRI) for detecting and measuring physiological processes within a patient.

Magnetic resonance spectroscopy and imaging techniques are generally known in the field of medical diagnostics and medical imaging. In general, MR techniques typically involve subjecting a patient to a uniform magnetic field, within which the spins of the magnetically responsive materials precess at a specific frequency depending on the strength of the magnetic field and the species of the magnetically responsive material. The uniform magnetic field also causes the poles of the spins of the magnetically responsive materials within the patient to preferentially align in the direction of the magnetic field. A superconducting, primary electromagnetic coil cooled with a cryostat filled with liquid helium may be used to produce this uniform magnetic field. Shim coils may also be used to provide fine tuning for an overall homogenous, uniform magnetic field within the bore of the MR scanner. Magnetic gradient coils may also be provided to vary the magnetic field spatially such that different spatial locations of magnetically responsive materials become associated with different precession or resonant frequencies. The magnetic fields generated by the magnetic gradient coils may be pulsed to create variations in the overall magnetic field within the bore in a slight, but predictable manner.

The patient is also then subjected to intermittent pulses at one or more radiofrequencies (RF) that tip the spins of the magnetically responsive materials into a plane that is transverse to the uniform magnetic field. Once these excitation RF pulses are discontinued, the spins of the magnetically responsive materials then realign with the uniform magnetic field. Magnetic resonance data may be collected during this realignment process, as the magnetically responsive materials emit a resonance signal. Distinct nuclear species of magnetically responsive materials can be identified as having distinct resonant frequencies when returning to the realigned state. The same RF coils may both transmit the RF pulses, and also receive the magnetic resonance data created by the spinning magnetically responsive materials responsive to the magnetic fields and these RF pulses. In some cases, dedicated RF coils are used to transmit RF pulses and separate RF coils are used in conjunction to detect the resonance signals.

Exemplary magnetically responsive materials within a patient include hydrogen (H), deuterium (2H) or carbon-13 (13C) atoms, whereby the difference in protons versus neutrons creates an electron cloud imbalance that renders the material responsive to magnetic fields. Different nuclear species have different imbalances, resulting in distinct spin frequencies that allows the difference species to be distinguished relative to others. When the responsive material, whether it is hydrogen or carbon-13 atoms, is a constituent of a molecule, the electron cloud of the molecule affects the magnetic field strength experienced by the responsive material. This variation in the effective magnetic field strength results in a small change to the precession frequency of the spins. This change to the precession frequency is manifested as a chemical shift that allows different molecules containing the responsive material to be distinguished from one another. For example, hydrogen atoms within the water molecule and hydrogen atoms within the lipid molecules have different spin precession frequency and thus resonance frequency under an uniform magnetic field, and this difference, the chemical shift, allows these two different molecules to be identified and potentially quantified within the body using Magnetic Resonance methods.

An exemplary MR system or MR scanner presently known in the art is GE Healthcare's 3 T GE MR750 scanner equipped with multinuclear spectroscopy hardware. Additional information regarding MR systems, imaging, and spectroscopy can also be found in U.S. Pat. Nos. 8,933,697; 9,283,317; 7,795,868; and 8,968,703, and U.S. Patent Application Publication No. 2019/0094316, which are incorporated herein by reference in their entireties.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One embodiment of the present disclosure generally relates to a method for detecting a metabolism of glucose by a patient. The method includes producing a magnetic field that acts upon the patient, then acquiring magnetic resonance data of deuterated water within the patient, where deuterated glucose has been administered to the patient, where the deuterated water is produced during the metabolism of the deuterated glucose by the patient, and where the magnetic resonance data is acquired at a resonant frequency of deuterium. The method further includes analyzing the magnetic resonance data acquired at the resonant frequency of deuterium, non-spectrally resolved, to generate a processed dataset. The method further includes constructing an image based on the processed dataset, where the metabolism of the glucose by the patient is detected via the constructed image.

Another embodiment generally relates to a magnetic resonance imaging (MRI) scanner configured to detect a metabolism of glucose by a patient. The MRI scanner includes a magnetic coil system configured to generate a magnetic field that acts upon the patient. An acquisition system is configured to acquire magnetic resonance data of deuterated water within the patient responsive to the magnetic field, where the deuterated water is produced during the metabolism of deuterated glucose administered to the patient, and where the magnetic resonance data is acquired at a resonant frequency of deuterium. A data analysis system is configured to analyze the magnetic resonance data acquired at the resonant frequency of deuterium, non-spectrally resolved, to generate a processed dataset. An image construction system is configured to construct an image based on the processed dataset. The metabolism of the glucose by the patient is detected via the constructed image.

Another embodiment generally relates to a method for detecting a metabolism of glucose by a patient. The method includes deuterating glucose such that deuterium is bound to the carbon atoms of the pyranose ring thereof, thereby producing deuterated glucose, then administering the deuterated glucose to the patient. The method further includes producing a magnetic field that acts upon the patient and acquiring magnetic resonance data of deuterated water within the patient, where the deuterated water is produced during the metabolism of the deuterated glucose by the patient, and where the magnetic resonance data is acquired only at a resonant frequency of deuterium, and specifically at the chemical shift of deuterated water. The method further includes analyzing the magnetic resonance data acquired at the resonant frequency of deuterium, non-spectrally resolved, to generate a processed dataset, then constructing an image based on the processed dataset. The metabolism of the glucose by the patient is detected via the constructed image.

In certain embodiments, the magnetic resonance data is acquired via gradient echo imaging.

In certain embodiments, the magnetic resonance data is collected for less than 10 minutes.

In certain embodiments, the magnetic resonance data is a delayed magnetic resonance data acquired a delay time after the deuterated glucose is administered to the patient, further comprising acquiring baseline magnetic resonance data of deuterated water within the patient before the deuterated glucose is metabolized by the patient, and wherein analyzing the magnetic resonance data includes subtracting the baseline magnetic resonance data the image from the delayed magnetic resonance data to generate the processed dataset. In further embodiments, the delay time is at least 10 minutes.

Certain embodiments further include analyzing the magnetic resonance data includes applying diffusion weighting.

In certain embodiments, the magnetic resonance data is acquired entirely after the deuterated glucose is administered to the patient.

In certain embodiments, the processed dataset on which the image is generated without spectrally resolving individual peaks in the deuterium spectrum.

In certain embodiments, the image is created without the use of data from ionizing radiation sources.

In certain embodiments, the acquisition system is configured to acquire the magnetic resonance data via gradient echo imaging. In further embodiments, the acquisition system acquires the magnetic resonance data for less than 10 minutes. In further embodiments, the magnetic resonance data is a delayed magnetic resonance data acquired a delay time after the deuterated glucose is administered to the patient, wherein the acquisition system is also configured to acquire baseline magnetic resonance data of naturally abundant deuterated water within the patient before the deuterated glucose metabolized by the patient, and wherein the data analysis system is further configured to subtract the baseline magnetic resonance data the image from the delayed magnetic resonance data to generate the processed dataset. In further embodiments, the delay time is at least 10 minutes.

In certain embodiments, the data analysis system is configured to analyze the magnetic resonance data via diffusion weighting. In further embodiments, the magnetic resonance data is acquired entirely after the deuterated glucose is administered to the patient.

In certain embodiments, the processed dataset on which the image is generated without spectrally resolving individual peaks in the deuterium spectrum.

In certain embodiments, the image is created without the use of data from ionizing radiation sources.

In certain embodiments, the magnetic resonance data is collected for less than 10 minutes, further comprising analyzing the magnetic resonance data acquired for the deuterated water using diffusion weighting before constructing the image, wherein the processed dataset on which the image is generated without spectrally without spectrally resolving individual peaks in the deuterium spectrum, and wherein the image is created without the use of data from ionizing radiation sources.

Various other features, objects and advantages of the disclosure will be made apparent from the following description taken together with the drawings.

BRIEF DESCRIPTION OF THE DRAWINGS

The present disclosure is described with reference to the following Figures.

DETAILED DISCLOSURE

Detection of changes in carbon metabolism is utilized in various imaging methods to diagnosis diseases. For example, fluorodeoxyglucose-positron emission tomography (FDG-PET), exploits the fact that many types of cancer cells have increased glucose uptake relative to "normal" cells, providing a basis for diagnostic image of primary and metastatic tumors. However, the inventor has recognized that PET imaging as a whole is limited to the analog of the biological substrate and cannot inform on the actual metabolism of the molecule by the patient. For example, the most commonly used PET agent, fluorodeoxyglucose or FDG is an analog of glucose, where a hydroxyl group of the glucose if replaced by fluorine-18. The result of this modification means that FDG can not be metabolized in the same manner as the unmodified glucose.

MR metabolic imaging with 13C (also referred to as carbon-13) enriched, but endogenous substrates, have also been used. The isotopic enrichment of a molecule does not, in general, change the chemical property of the molecule. Thus, molecules enriched with 13C (i.e. carbon-12 substituted by carbon-13C) can be metabolized by the cells in the same manner as the non-enriched molecules. However, the low sensitivity of 13C nuclei makes this technique impractical without a means to drastically increase the nuclear polarization of the imaging substrate, such as the dissolution Dynamic Nuclear Polarization method (DNP). Unfortunately, the dissolution DNP methods presently known in the art require costly and complex instrumentation. Moreover, dissolution DNP methods are typically suitable only for small molecules that have long longitudinal relaxation time (commonly referred to as T1 within the field). Molecules such as glucose and fatty acids have 13C relaxation times (T1s) that are too short for in vivo imaging of the substrates and their metabolic products with dissolution DNP.

Using a deuterium (2H) enriched metabolic substrate to assess carbon metabolism has recently gained interest in the MR metabolic imaging community. The feasibility of using deuterated glucose for investigation of glucose consumption rate and TCA cycle flux was demonstrated in vivo in an animal model (Lu, M. et al. J. Cereb. Blood Flow Metab. 2017 37(11):3518-3530). Using deuterated glucose to map metabolism in normal human brain and also to investigate metabolic changes in brain tumor was recently demonstrated as well (De Feyter, H M. et al. Sci Adv. 2018 4(8):eaat7314).

Deuterium metabolic imaging (DMI) does not require expensive additional instrumentation such as cyclotron or polarizer for preparation of the agent (many deuterium enriched molecules are available from specialized vendors), and its safety at the doses administered in these studies is well established. However, like 13C MR without hyperpolarization, the sensitivity of DMI is low due to the much lower gyromagnetic ratio of 2H as compared to 1H, as well as the relatively low concentrations of metabolites as compared to endogenous water and fat molecules. One advantage of DMI as compared to 13C MR (without hyperpolarization) is that the T1 of deuterium is relatively short, thus more signal averaging can be performed within a given scan time. However, to acquire spatially resolved maps of metabolites generated from deuterated glucose in vivo (such as lactate and glutamate+glutamine), the scan times on the order of 10 minutes or more are still necessary. Therefore, methods to increase the sensitivity of DMI are still needed to make it more suitable for routine clinical imaging.

Figure 2:
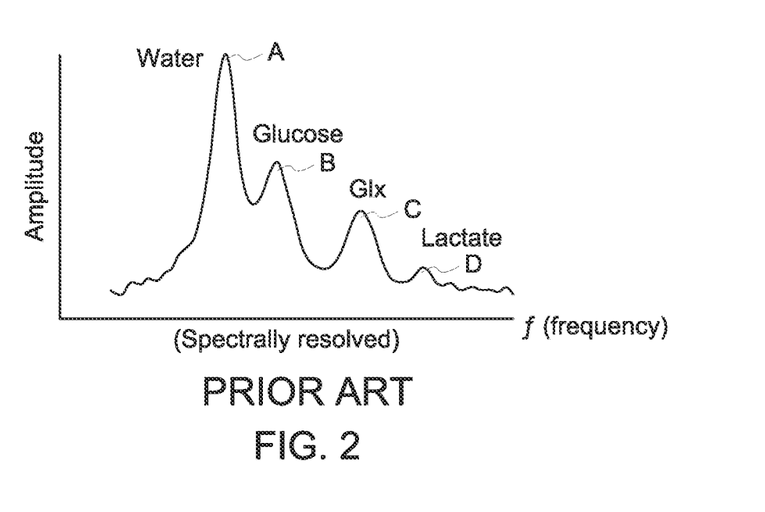
FIG. 2 is a chart exemplifying magnetic resonance data acquired from an MRI, with the data shown spectrally resolved to identify amplitudes of metabolites at various chemical shifts as known in the prior art.

To date, DMI has been performed using MR spectroscopic acquisition following the administration of a deuterated metabolic substrate. The spectroscopic mode allows the resonances from deuterated water, the infused 2H enriched glucose, and its metabolites to be resolved and quantified independently (see FIG. 2.). Specifically, this spectral resolution is obtained by performing Fourier analysis on the incoming magnetic resonance data, acquired over a sufficiently long duration (in time) of the free induction decay (FID). The result is a spectrum of peaks that originated from deuterated molecules that have different chemical shifts. The inventor has recognized that MR spectroscopic acquisition, however, is time consuming since a long acquisition window is required to capture a sufficient long portion of the FID. Typically, no encoding gradient is utilized during readout, thus the total scan time can be prohibitive long for spatially resolved data.

Also, due to the small chemical shift difference between different deuterated species and broad line-shape of these peaks contributed by the quadruple moment of deuterium nuclear spin, substantial overlap between the peaks can often be observed and it may be difficult to resolve and accurately quantify the different deuterium resonances. Additionally, perhaps the biggest obstacle remains the low signal to noise ratio of the acquired magnetic resonance data, especially for the less concentrated metabolites such as lactate.

Figure 1:
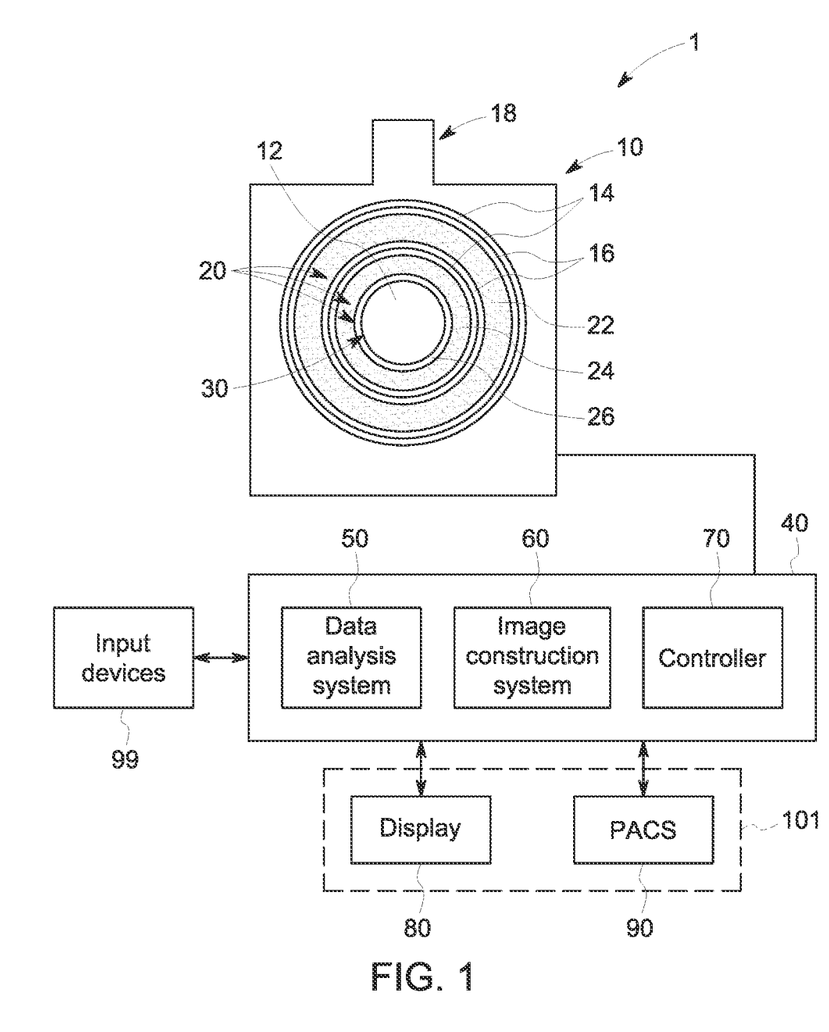
FIG. 1 is a schematic depiction of an exemplary magnetic resonance imaging (MRI) scanner and system configured according to the present disclosure.

FIG. 1 depicts an exemplary system 1 for acquiring magnetic resonance data according to the present disclosure, which is useful for detecting glucose metabolism in a patient. The system 1 includes a magnetic resonance (MR) scanner 10, for example GE Healthcare's 3T GE MR750. The MR scanner 10 accepts a patient within the scanner bore 12 in a manner known in the art. As discussed above in the Background section, the MR scanner 10 includes a magnetic coil system 20 including a primary electromagnetic coil 22, magnetic gradient coils 24, and radio frequency (RF) coils 26. The RF coils 26 also form a portion of the acquisition system 30, functioning in a manner presently known in the art. Thermal insulation 14 and layers of cryostats filled with liquid helium 16 are also shown surrounding the primary electromagnetic coil 22, again as presently known in the art. Services connections 18 to the MR scanner 10 are also provided, for example to provide communication, power, and coolant passage to and from the MR scanner 10 in a manner known in the art.

The MR scanner 10 is provided in communication with a console 40, which is presently shown to receive communication from input devices 99 (e.g. keyboards, mice, and other control devices), and also with output devices 101, shown here as a display 80 and picture archiving and communication system (PACS) 90. The console 40 presently shown incorporates a data analysis system 50, image construction system 60, and controller 70, though it will be recognized that these systems and controller may be provided in separate forms and/or in differing combinations.

In the example shown, the data analysis system 50 is configured to analyze the magnetic resonance data received from the MR scanner 10, such as magnetic resonance data acquired at the resonant frequency of deuterium, and to generate a processed data set without spectrally resolving the magnetic resonance data. The image construction system 60 is then configured to receive the processed data set from the data analysis system 50 and to construct 2-D or 3-D images based on this processed data set. It will then be recognized that the metabolism of the glucose by the patient can then be detected via the constructed images, as discussed further below.

Figure 6:
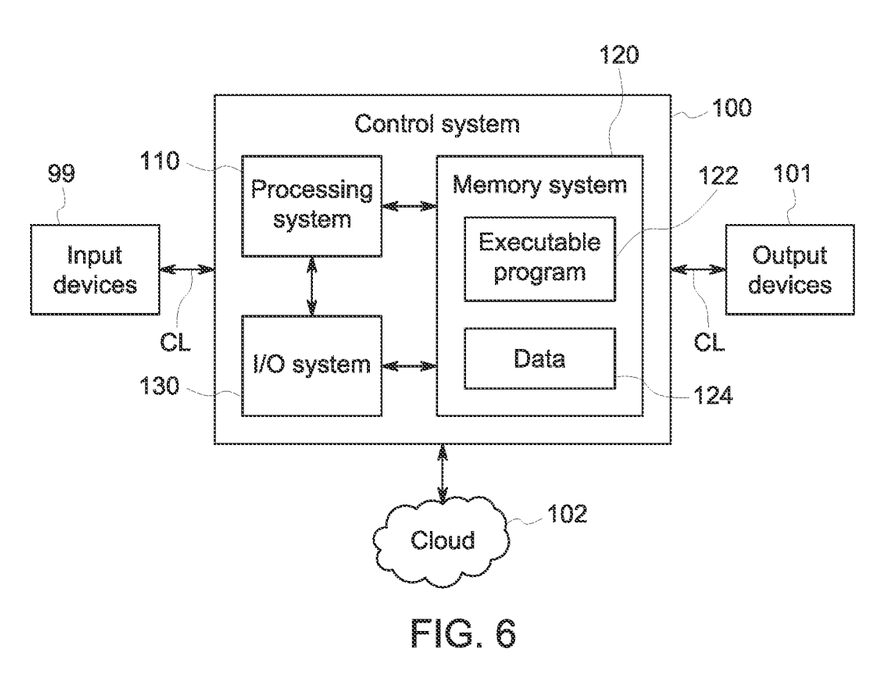
FIG. 6 is a schematic representation of an exemplary control system as may be incorporated within the system shown in FIG. 1.

The console 40 is also shown as incorporating a controller 70, which serves to control the functions of the MR scanner 10 in a manner known in the art. FIG. 6 depicts an exemplary control system 100 that may be incorporated within the console 40, or separately within one or more of the data analysis system 50, image construction system 60, and/or controller 70 if separate hardware devices rather than modules within a common console 40, to perform the respective functions thereof. In the case of a console 40 having the data analysis system 50, image construction system 60, and/or controller 70 as software based modules therein, these individual modules may be stored within the memory system 120, executable by the processing system 110, for example. Through an exemplary control system 100 is provided herein, the console 40 may be of the type presently known in the art, including that used in conjunction with GE Healthcare's 3T GE MR750 MR Scanner, for example.

Certain aspects of the present disclosure are described or depicted as functional and/or logical block components or processing steps, which may be performed by any number of hardware, software, and/or firmware components configured to perform the specified functions. For example, certain embodiments employ integrated circuit components, such as memory elements, digital signal processing elements, logic elements, look-up tables, or the like, configured to carry out a variety of functions under the control of one or more processors or other control devices. The connections between functional and logical block components are merely exemplary, which may be direct or indirect, and may follow alternate pathways.

In certain examples, the control system 100 communicates with each of the one or more components of the console 40 and/or system 1 via a communication link CL, which can be any wired or wireless link. The control module 100 is capable of receiving information and/or controlling one or more operational characteristics of the system 1 and its various sub-systems by sending and receiving control signals via the communication links CL. In one example, the communication link CL is a controller area network (CAN) bus; however, other types of links could be used. It will be recognized that the extent of connections and the communication links CL may in fact be one or more shared connections, or links, among some or all of the components in the system 1. Moreover, the communication link CL lines are meant only to demonstrate that the various control elements are capable of communicating with one another, and do not represent actual wiring connections between the various elements, nor do they represent the only paths of communication between the elements. Additionally, the system 1 may incorporate various types of communication devices and systems, and thus the illustrated communication links CL may in fact represent various different types of wireless and/or wired data communication systems.

The control system 100 may be a computing system that includes a processing system 110, memory system 120, and input/output (I/O) system 130 for communicating with other devices, such as input devices 99 and output devices 101, either of which may also or alternatively be stored in a cloud 102. The processing system 110 loads and executes an executable program 122 from the memory system 120, accesses data 124 stored within the memory system 120, and directs the system 1 to operate as described in further detail below.

The processing system 110 may be implemented as a single microprocessor or other circuitry, or be distributed across multiple processing devices or sub-systems that cooperate to execute the executable program 122 from the memory system 120. Non-limiting examples of the processing system include general purpose central processing units, application specific processors, and logic devices.

The memory system 120 may comprise any storage media readable by the processing system 110 and capable of storing the executable program 122 and/or data 124. The memory system 120 may be implemented as a single storage device, or be distributed across multiple storage devices or sub-systems that cooperate to store computer readable instructions, data structures, program modules, or other data. The memory system 120 may include volatile and/or non-volatile systems, and may include removable and/or non-removable media implemented in any method or technology for storage of information. The storage media may include non-transitory and/or transitory storage media, including random access memory, read only memory, magnetic discs, optical discs, flash memory, virtual memory, and non-virtual memory, magnetic storage devices, or any other medium which can be used to store information and be accessed by an instruction execution system, for example.

The inventor has developed the presently disclosed systems and methods for detecting glucose metabolism in a patient, which unlike the methods presently known in the art do not require a spectrally resolved acquisition of the magnetic resonance data. Specifically, the inventor has recognized that it is possible to assess the consumption of glucose in the tissue with deuterium MR imaging without having to quantify the amount of deuterium enriched metabolites produced during the metabolic process, such as glutamate, glutamine, and lactate. Instead, it is possible to measure the signal from the water generated during glycolysis. If the glucose is deuterated at the carbons in the pyranose ring (in addition to, or instead of other locations commonly done for DMI), then the water molecules generated from the deuterated glucose would be enriched with deuterium. Indeed, for each molecule of glucose consumed by the cellular metabolism, two molecules of water are generated as product along with two molecules of pyruvate.

Figure 5:
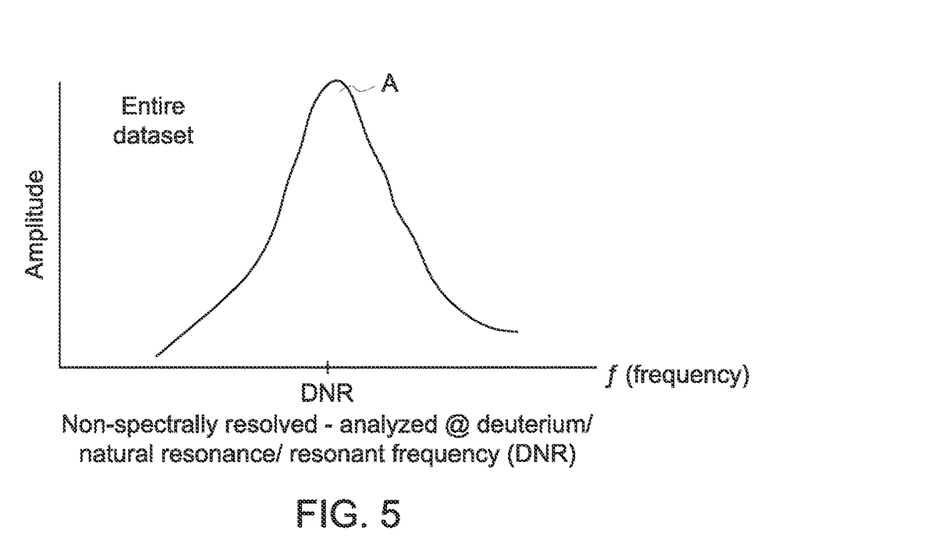
FIG. 5 is a chart depicting magnetic resonance data of deuterated water, without spectrally resolving signals from any deuterated metabolites, analyzed at a deuterium natural resonance or resonant frequency according to the present disclosure.

Therefore, the changes in the deuterated water (HDO) signal may also be used to assess changes in glucose uptake and glycolytic flux during the metabolic process. Instead of acquiring spectrally resolved 2H signal from all the deuterium resonances to quantify deuterium enriched lactate and glutamate/glutamine, the presently disclosed systems and methods only require imaging the deuterated water resonance. By acquiring magnetic resonance data from only the deuterated water resonance (see FIG. 5, for example), the overall process of data acquisition and analysis is substantially simplified and more efficient, since spectroscopic data is required.

Since deuterium is 0.015% naturally abundant, there will be a background deuterated water signal even without any administered deuterium enriched glucose. To obtain the imaging contrast manifested from the glucose metabolism, one method of monitoring the metabolic process is to perform a baseline scan prior to administering the deuterated glucose. Once the deuterated glucose has been administered to the patient and sufficient time has passed for the metabolic process to take place, subsequent delayed magnetic acquisition data may be collected to detect the deuterated water produced by the glucose being metabolized by the tissue. The baseline magnetic resonance acquisition data can then be subtracted from the delayed magnetic resonance acquisition data to remove the impact of naturally abundant deuterium and to identify which tissues have metabolized the glucose. This subtraction may be carried out in a manner known in the art, but as stated above uses deuterated water rather than spectrally resolving metabolites.

Figure 3:
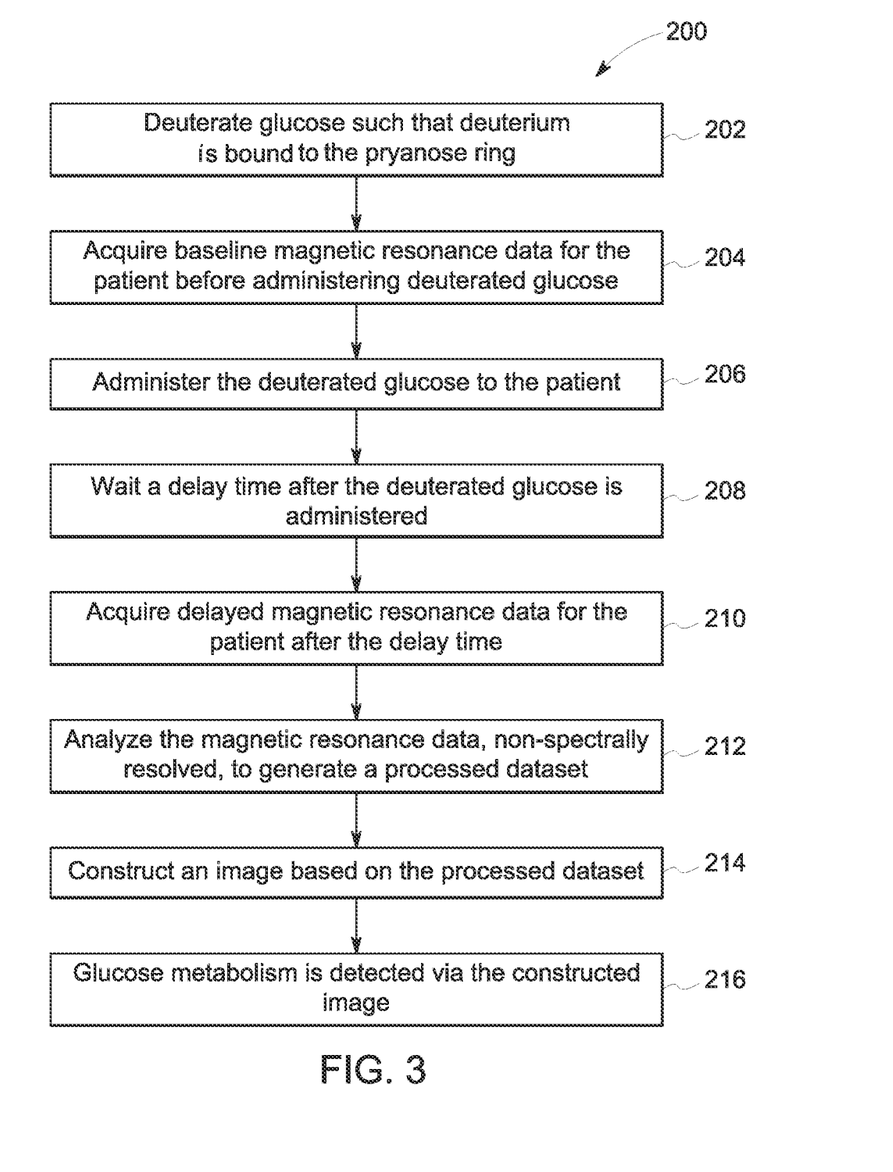
FIG. 3 is an exemplary method for detecting glucose metabolism according to the present disclosure.

FIG. 3 generally depicts this process as exemplary method 200. The method 200 begins with deuterating glucose in step 202 such that deuteriums are bound to carbons of the pyranose ring of the glucose molecule. Step 204 then provides for acquiring base line magnetic resonance data for the patient before administering the deuterated glucose, using techniques presently known in the art. It will be recognized that the baseline magnetic resonance data may also be acquired after the deuterated glucose is administered, provided it is only shortly thereafter. Since glucose uptake and metabolism generally takes on the order of 10s of minutes, step 204 in certain embodiments may be taken within 5 minutes (as a non-limiting example), of administering the glucose, for example, with only a minimal contribution from the HDO generated from the administered glucose. The deuterated glucose is then administered to the patient in step 206, and the process waits for a delayed time until after the deuterated glucose has been administered as step 208. After this delay time has elapsed, step 210 provides for acquiring delayed magnetic resonance data for the patient after the delay time, which is essentially repeating the step of 204 now that the deuterated glucose has been at least partially metabolized by the patient. Step 210 may be repeated to provide kinetic information related to glucose metabolism.

Step 212 provides for analyzing the magnetic resonance data, non-spectrally resolved, to generate a processed data set. In the method 200, this analysis includes subtracting the base line magnetic resonance data collected in step 204 from the delayed magnetic resonance data in step 210, resulting in the cancellation of naturally abundant deuterium within the patient such that the only source of deuterium visible in the data is that deriving from the deuterating glucose administered to the patient in step 206. An image is then constructed based on the processed data set in step 214, whereby glucose metabolism may be detected in step 216 via the constructed image in a manner known in the art.

In short, by eliminating the need to spectrally resolve all individual metabolites of deuterated glucose as presently performed for DMI, significant time and cost saves can be obtained. Since there is no need to spectrally resolve among multiple metabolites, the acquisition window for each FID can be much shorter and less overall data need to be sampled. Moreover, standard MRI methods to encode spatial information during readout can be used, thus speed up the scans. But perhaps most importantly is the fact that deuterated water signal is much larger than that of the metabolites, therefore extensive signal averaging may not be required as it is currently done in DMI with MR spectroscopic methods. This equates to less time for the patient in the scanner, for example a reduction from the 20 minutes or more using methods presently known in the art down to less than 10 minutes, or even 3-7 minutes depending on the patient, anatomy being imaged, and/or the like, for example.

Less processing is also required, therefore reducing the time to produce the final image. This, coupled with the reduced patient time in the scanner, improves patient throughput and the efficiency of using expensive and complicated hardware. As stated above, it also leads to an improvement in the quality of the data, for example by improving the signal to noise ratio of analyzing magnetic resonance data collected only at the deuterated water resonant frequency, versus signals spectrally resolved for multiple metabolites.

While this baseline acquisition method using deuterated water signifies an improvement over the methods presently known in the art, the inventor has identified further improvements to be realized through the detection of deuterated water for imaging glucose uptake. In particular, conducting a baseline scan requires more time for the patient to be in the MR scanner. Additionally, this is baseline scan is separated in time from the delayed acquisition after the glucose is administered. Thus, the patient must either remain in scanner for the entire delay period after the glucose administration (often 20 minutes or more), increasing discomfort and system downtime, or be removed and returned to the scanner after another patient is imaged. Similarly, the use of two datasets that are subtracted may lead to motion error due to patient movement or other issues during or between the two scans.

The inventor has recognized that rather than subtracting a baseline magnetic resonance dataset, it is instead possible to isolate the HDO signal generated by the glucose metabolism from the HDO signal from the background water by applying diffusion weighting during the scan. In particular, the water molecules produced from the metabolism of the deuterated glucose will be intracellular, at least when the water molecule is first generated. In contrast, a large portion of the background water molecules (i.e., those containing naturally abundant deuterium) are extracellular. Water molecules inside the cells have more restricted diffusion than those outside the cells, which are relatively more mobile. In this respect, the newly produced (deuterated) water from the deuterated glucose at least initially reside in compartments of the cytosol, and are more restricted in mobility as well.

Therefore, one diffusion weighted scan using the HDO signal after administration of deuterated glucose can be sufficient to create the contrast needed to detect increased glucose uptake and glycolysis in diseased tissues such as tumors.

Figure 4:
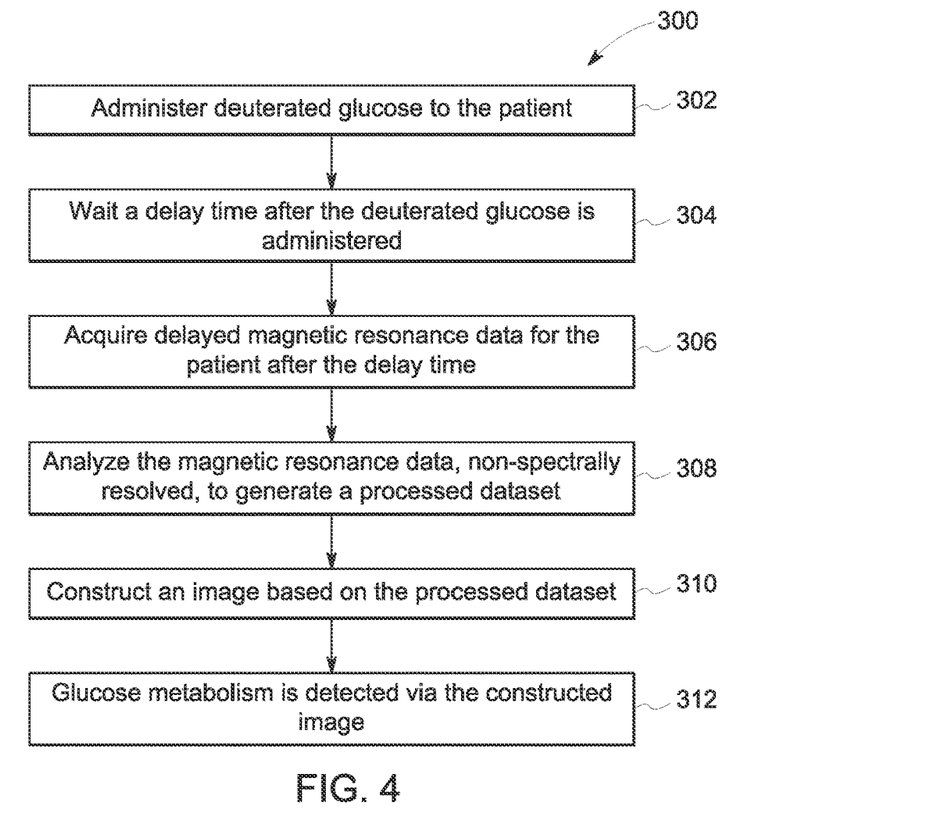
FIG. 4 is another exemplary method for detecting glucose metabolism according to the present disclosure.

An exemplary method 300 for detecting glucose metabolism using diffusion weighted scan techniques is shown in FIG. 4. The method 300 begins by administering deuterated glucose to the patient in step 302, then waiting a delay time after the deuterated glucose is administered in step 304. Step 306 provides for acquiring delayed magnetic resonance data for the patient after the delay time elapsed in step 304. This magnetic resonance data is then analyzed in step 308, non-spectrally resolved, to generate a processed data set. As with step 212 in the method 200 of FIG. 3, the analysis of step 308 is performed on a data set that is acquired using MR imaging acquisition mode, rather than MR spectroscopic acquisition mode. An image is then constructed based on the processed data set from step 308 in step 310, whereby glucose metabolism can then again be detected via the constructed image in step 312 in a manner known in the art.

It is further noteworthy that when imaging an HDO signal with a non-spectrally resolved imaging method, the off-resonance peak from the administered deuterated glucose will contribute to the total signal and may be a source for chemical shift artifacts. However, since many tumors are known to have increased glucose update, the increase in deuterated glucose signal may actually enhance the contrast of the tumors versus background signal from "normal" tissue. Additionally, the spatial resolution is likely to be relatively coarse for deuterium imaging, and the frequency difference between HDO and deuterated glucose is quite small (~20 Hz at 3 T). Therefore, the chemical shift artifacts will in many circumstances be negligible.

In this manner, the presently disclosed systems and methods provide substantial improvements over those presently known in the art. As discussed above, these improvements include imaging glucose metabolism without ionization radiation associated with FDG-PET, and doing so more efficiently by directly imaging the deuterated water molecule generated by the glucose metabolism instead of the acquiring spectrally resolved deuterium spectra following administering a dose of deuterium labeled glucose. Moreover, diffusion weighted imaging of deuterated water can create imaging contrast without the need for time consuming and error-inducing baseline dataset subtractions.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. Certain terms have been used for brevity, clarity, and understanding. No unnecessary limitations are to be inferred therefrom beyond the requirement of the prior art because such terms are used for descriptive purposes only and are intended to be broadly construed. The patentable scope of the invention is defined by the claims and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

What is claimed is:

1. A method for detecting an uptake and metabolism of glucose by a patient, the method comprising:
   producing a magnetic field that acts upon the patient;
   acquiring, non-spectrally resolved, magnetic resonance data of deuterated water within the patient, wherein deuterated glucose has been administered to the patient, wherein the deuterated water is produced during the metabolism of the deuterated glucose by the patient, and wherein the magnetic resonance data is acquired at a resonant frequency of deuterated water;
   analyzing the magnetic resonance data acquired at the resonant frequency of deuterated water, non-spectrally resolved, to generate a processed dataset; and
   constructing an image based on the processed dataset;
   wherein the metabolism of the glucose of the patient is detected via the constructed image.

2. The method according to claim 1, wherein the magnetic resonance data is acquired via gradient echo imaging.

3. The method according to claim 1, wherein the magnetic resonance data is collected for less than 10 minutes.

4. The method according to claim 1, wherein the magnetic resonance data is a delayed magnetic resonance data acquired a delay time after the deuterated glucose is administered to the patient, further comprising acquiring baseline magnetic resonance data of deuterated water within the patient before the deuterated glucose is metabolized by the patient, and wherein analyzing the magnetic resonance data includes subtracting the baseline magnetic resonance data from the delayed magnetic resonance data to generate the processed dataset.

5. The method according to claim 4, wherein the delay time is at least 10 minutes.

6. The method according to claim 1, wherein the magnetic resonance data of the deuterated water is acquired with diffusion weighting.

7. The method according to claim 6, wherein the magnetic resonance data is acquired entirely after the deuterated glucose is administered to the patient.

8. The method according to claim 1, wherein the processed dataset on which the image is generated without spectrally resolving individual peaks in the deuterated water spectrum.

9. The method according to claim 1, wherein the image is created without generating ionizing radiation.

10. A magnetic resonance imaging (MRI) scanner configured to detect a metabolism of glucose by a patient, the MRI scanner comprising:
    a magnetic coil system configured to generate a magnetic field that acts upon the patient;
    an acquisition system configured to acquire magnetic resonance data, non-spectrally resolved, of deuterated water within the patient responsive to the magnetic field, wherein the deuterated water is produced during the metabolism of deuterated glucose administered to the patient, and wherein the magnetic resonance data is acquired at a resonant frequency of deuterated water;
    a data analysis system configured to analyze the magnetic resonance data acquired at the resonant frequency of deuterated water, non-spectrally resolved, to generate a processed dataset; and
    an image construction system configured to construct an image based on the processed dataset;
    wherein the uptake and metabolism of the glucose of the patient is detected via the constructed image.

11. The MRI scanner according to claim 10, wherein the acquisition system is configured to acquire the magnetic resonance data via gradient echo imaging.

12. The MRI scanner according to claim 10, wherein the acquisition system acquires the magnetic resonance data for less than 10 minutes.

13. The MRI scanner according to claim 10, wherein the magnetic resonance data is a delayed magnetic resonance data acquired a delay time after the deuterated glucose is administered to the patient, wherein the acquisition system is also configured to acquire baseline magnetic resonance data of deuterated water within the patient before the deuterated glucose is metabolized by the patient, and wherein the data analysis system is further configured to subtract the baseline magnetic resonance data from the delayed magnetic resonance data to generate the processed dataset.

14. The MRI scanner according to claim 13, wherein the delay time is at least 10 minutes.

15. The MRI scanner according to claim 10, wherein the magnetic resonance data of the deuterated water is acquired with diffusion weighting.

16. The MRI scanner according to claim 15, wherein the magnetic resonance data is acquired entirely after the deuterated glucose is administered to the patient.

17. The MRI scanner according to claim 10, wherein the processed dataset on which the image is generated without spectrally resolving individual peaks in the deuterated water spectrum.

18. The MRI scanner according to claim 10, wherein the MRI scanner is configured to create the image without generating ionizing radiation.

19. A method for detecting a metabolism of glucose by a patient, the method comprising:
    deuterating glucose such that deuterium is bound to carbons on a pyranose ring thereof, thereby producing deuterated glucose;
    administering the deuterated glucose to the patient; producing a magnetic field that acts upon the patient;
    acquiring magnetic resonance data, non-spectrally resolved, of deuterated water within the patient, wherein the deuterated water is produced during the metabolism of the deuterated glucose by the patient, and wherein the magnetic resonance data is acquired only at a resonant frequency of deuterated water and by using diffusion weighting;
    analyzing the magnetic resonance data acquired at the resonant frequency of deuterated water, non-spectrally resolved, to generate a processed dataset; and
    constructing an image based on the processed dataset;
    wherein the metabolism of the glucose of the patient is detected via the constructed image.

20. The method according to claim 19, wherein the magnetic resonance data is collected for less than 10 minutes, further comprising analyzing the magnetic resonance data acquired for the deuterated water using diffusion weighting before constructing the image, wherein the processed dataset on which the image is generated without spectrally resolving individual peaks in the deuterated water spectrum, and wherein the image is created without generating ionizing radiation.

21. The method according to claim 1, wherein the deuterated glucose administered to the patient has been deuterated at one or more carbons of a pyranose ring thereof.

22. A system comprising the MRI scanner according to claim 10 and the deuterated glucose configured to be administered to the patient, wherein the deuterated glucose has been deuterated at one or more carbons of a pyranose ring thereof.

* * * * *